(12) United States Patent
Chadderdon, III et al.

(10) Patent No.: US 9,801,553 B2
(45) Date of Patent: Oct. 31, 2017

(54) SYSTEM, METHOD, AND COMPUTER PROGRAM PRODUCT FOR THE REAL-TIME MOBILE EVALUATION OF PHYSIOLOGICAL STRESS

(71) Applicant: DESIGN INTERACTIVE, INC., Orlando, FL (US)

(72) Inventors: George Chadderdon, III, Oviedo, FL (US); Brent Winslow, Oviedo, FL (US); Sara Dechmerowski, Orlando, FL (US); David Jones, Orlando, FL (US)

(73) Assignee: Design Interactive, Inc., Orlando, FL (US)

( * ) Notice: Subject to any disclaimer, the term of this patent is extended or adjusted under 35 U.S.C. 154(b) by 394 days.

(21) Appl. No.: 14/497,763

(22) Filed: Sep. 26, 2014

(65) Prior Publication Data

US 2016/0089038 A1    Mar. 31, 2016

(51) Int. Cl.
*A61B 5/0205*    (2006.01)
*A61B 5/11*    (2006.01)
(Continued)

(52) U.S. Cl.
CPC ........ *A61B 5/02055* (2013.01); *A61B 5/0531* (2013.01); *A61B 5/1118* (2013.01);
(Continued)

(58) Field of Classification Search
CPC ... A51B 5/0205; A51B 5/1118; A51B 5/7264; A51B 5/7282; A51B 5/165;
(Continued)

(56) References Cited

U.S. PATENT DOCUMENTS 8,673,647 B2    3/2014 Tanaka et al.
8,747,311 B2    6/2014 Barr
(Continued)

FOREIGN PATENT DOCUMENTS

CN    EP 2060228 A1 *  5/2009   ........... A61B 5/0008

OTHER PUBLICATIONS

Raij et al., mStress: "Supporting Continous Collection of Objective and Subjective Measures of Psychosolcial Stress on Mobile Devices", ACM Wireless Health Conference Oct. 5-7, 2010 , pp. 1-10.*

(Continued)

*Primary Examiner* — Gary Jackson
*Assistant Examiner* — Boniface N Nganga
(74) *Attorney, Agent, or Firm* — Terry M. Sanks, Esq.; Beusse Wolter Sanks & Maire, PLLC (57) ABSTRACT

A system is disclosed including a measuring device comprising sensors configured to collect data from a user based on the sensor being at least one of in contact with and proximate to a section of skin of the user, a stress feature analyzer configured to determine a cardiovascular activity feature of the user, a skin conductance feature of the user, movement of the user, and skin temperature of the user based on the data collected with the measuring device, and a stress classifier configured to classify and report stress experienced by the user based on at least one of one feature selected from the cardiovascular activity feature and the skin conductance feature, and two features including a combination of the cardiovascular activity feature and the skin conductance feature, wherein when the skin temperature of the user exceeds a defined threshold, the stress classifier ceases to classify the stress experienced by the user. A method and a non-transitory processor readable storage medium are also disclosed.

20 Claims, 7 Drawing Sheets

(51) Int. Cl.
*A61B 5/00* (2006.01)
*A61B 5/16* (2006.01)
*A61B 5/053* (2006.01)
A61B 5/01 (2006.01)

(52) U.S. Cl.
CPC ............ *A61B 5/165* (2013.01); *A61B 5/6898* (2013.01); *A61B 5/7264* (2013.01); *A61B 5/7282* (2013.01); *A61B 5/0022* (2013.01); *A61B 5/01* (2013.01); *A61B 5/6802* (2013.01); *A61B 5/742* (2013.01); *A61B 5/7475* (2013.01)

(58) Field of Classification Search
CPC ... A51B 5/6898; A51B 5/0531; A51B 5/6802; A51B 5/742; A51B 5/01; A51B 5/7475; A51B 5/0022
USPC ................................ 600/300–301, 483, 595
See application file for complete search history.

(56) References Cited

U.S. PATENT DOCUMENTS

| | | | | |
|---|---|---|---|---|
| 2003/0139654 A1* | 7/2003 | Kim | ................... | A61B 5/02405 600/300 |
| 2003/0166996 A1* | 9/2003 | Kim | ...................... | A01K 29/00 600/300 |
| 2005/0154264 A1* | 7/2005 | Lecompte | ............ | A61B 5/4884 600/300 |
| 2006/0010010 A1* | 1/2006 | Wiegand | .............. | A61B 5/0059 705/2 |
| 2010/0302000 A1 | 12/2010 | Szymkkowiak et al. | | |
| 2013/0281798 A1 | 10/2013 | Rau et al. | | |

OTHER PUBLICATIONS

Autosense: "A Wireless Sensor System to Quantify Personal Exposure to Physchosocila Stress and Addictive Substances in Natural Enviroments", Wayback Machine, Oct. 17, 2011, pp. 1-48.*
Chernbumroong et al., "Activity classification using a single wrist-worn accelerometer", Sep. 2011, pp. 1-6.
Alamudun et al., "Removal of Subject-Dependent and Activity-Dependent Variation in Physiological Measures of Stress", In Pervasive Computing Technologies for Healthcare (PervasiveHealth), 2012, 6th International Conference on (pp. 115-122). IEEE.
Bakker et al., "What's your current stress level? Detection of stress patterns from GSR sensor data" In Data Mining Workshops (ICDMW), 2011, IEEE 11th International Conference on (pp. 573-580). IEEE.
De Santos Sierra et al., "Real-Time Stress Detection by Means of Physiological Signals", Group of Biometrics, Biosignals and Security Universidad Politécnica de Madrid, Spain, 2011, 24-44.
Plarre et al., "Continuous Inference of Psychological Stress from Sensory Measurements Collected in the Natural Environment", In Information Processing in Sensor Networks (IPSN), 2011, 10th International Conference on (pp. 97-108). IEEE.
Sun et al., "Activity-aware Mental Stress Detection Using Physiological Sensors", In Mobile Computing, Applications, and Services 2012, (pp. 211-230). Springer Berlin Heidelberg.

* cited by examiner

SYSTEM, METHOD, AND COMPUTER PROGRAM PRODUCT FOR THE REAL-TIME MOBILE EVALUATION OF PHYSIOLOGICAL STRESS

BACKGROUND

Embodiments relate to detecting stress in an individual and, more particularly, to a method and system for continuous classification of physiological stress in a mobile environment.

Though mobile health applications and wearable physiological sensors have the potential to analyze and present meaningful data to better manage and optimize general health and specific health conditions of an individual, such applications currently simply collect data and produce readouts of the collected data. For example, wearable devices are now able to track fitness-related metrics, such as, but not limited to, distance walked or run, calorie consumption, heartbeat rate, and quality of sleep.

Wearable physiological sensors provide quantifiable data in real time that may correlate with stress (such as heart rate variability and electrodermal activity), but these sensors are also activated by other inputs such as temperature and physical activity. Individual differences (e.g., age, gender, health status) and daily activities (e.g., physical movements, environmental changes) pose a complex problem in achieving an accurate classifier for stress.

There is a growing need to support the classification of physiological and psychological states when an individual is in a natural environment, as opposed to a controlled environment, such as an examination room or laboratory. Detecting and addressing stress is a key measure for mobile health applications, but the main challenge in addressing this need is an inability to classify stress in a mobile environment in real time. Current state of the art methods for stress monitoring are laboratory-based (not mobile) and episodic in nature (e.g. self report). Therefore individuals would benefit from a system and method that can discriminate between physiological stress and other (normal) psychological states of the user to provide for an accurate, quantitative classifier for continuous and objective real-time stress assessment.

SUMMARY

Embodiments relate to a system, method, and computer program product for continuous classification of physiological stress in a mobile environment. The system comprises a measuring device comprising at least one sensor configured to collect data from a user based on the sensor being at least one of in contact with and proximate to a section of skin of the user. The system further comprises a stress feature analyzer configured to determine at least one of cardiovascular activity of the user, skin conductance of the user, movement of the user, and skin temperature of the user based on data collected with the measuring device. The system also comprises a stress classifier configured to classify and report stress based on at least one of the cardiovascular activity, the skin conductance, and a combination of the cardiovascular activity and the skin conductance, wherein when at least one of skin temperature and movement of the user exceeds a defined threshold, the stress classifier ceases to classify stress.

The method comprises collecting, in real-time, at least one of cardiovascular activity data of a user and skin conductance data of the user in addition to movement data of the user and skin temperature data of the user with a wearable sensor array in proximity with a section of skin of the user. The method further comprises identifying, in real-time, when stress is experienced by the user based on at least one of the cardiovascular activity data collected and the skin conductance data collected wherein when at least one of the movement data and the skin temperature data exceeds a predefined threshold stress is not identified with a mobile device in communication with the wearable sensor array. The method also comprises classifying, in real time, an amount of stress experienced with a stress classifier, and reporting at least to the user when stress is experienced.

The computer program product is a non-transitory processor readable storage medium, providing an executable computer program product, the executable computer program product comprising a computer software code. When executed on a processor, the code causes the processor to identify, in real-time, when stress is experienced by the user based on at least one of cardiovascular activity data collected and skin conductance data collected with a wearable sensor array proximate a section of skin of the user. The processor is also caused to cease to identify, in real-time, when stress is experienced when at least one of movement data collected and the skin temperature data collected with the wearable sensor array proximate the section of skin of the user exceeds a predefined threshold. The processor is also caused to classify, in real time, an amount of stress experienced, and report at least to the user when stress is experienced.

BRIEF DESCRIPTION OF THE DRAWINGS

A more particular description of embodiments briefly described above will be rendered by reference to specific embodiments thereof that are illustrated in the appended drawings. Understanding that these drawings depict only typical embodiments and are not therefore to be considered limiting of its scope, embodiments will be described and explained with additional specificity and details through the use of the accompanying drawings in which.

DETAILED DESCRIPTION

Reference will be made below in detail to embodiments, non-limiting examples of which are illustrated in the accompanying drawings. Wherever possible, the same reference numerals used throughout the drawings refer to the same or like parts.

Embodiments solve problems in the art by providing a method and system for collecting, classifying, and presenting stress data for therapy support, either in a controlled setting such as a laboratory or clinic, or in a natural environment, by which is meant the setting of ordinary daily human activities (outside a lab or clinic). Thus, in the natural environment, events or stimuli which may create stress for an individual or user are unknown in advance and are not necessarily being controlled by the individual or another individual or entity, as such events are simply occurring as they normally would.

Persons skilled in the art will recognize that an apparatus, such as a data processing system, including a CPU, memory, I/O, program storage, a connecting bus, and other appropriate components, could be programmed or otherwise designed to facilitate the practice of a method of an embodiment. Such a system would include appropriate program means, or as disclosed herein, mobile application, for executing the method.

Broadly speaking, a purpose of an embodiment is to provide a physiological data collection and classification system based on information obtained from a user using wearable sensors and a mobile application to evaluate data that may be collected in a natural environment, and/or in a more controlled environment such as a lab or clinic. To facilitate an understanding of the embodiments disclosed herein, it is described hereinafter with reference to specific implementations thereof. Embodiments may be described in the general context of computer-executable instructions, such as program modules, being executed by any device, such as but not limited to a computer, designed to accept data, perform prescribed mathematical and/or logical operations usually at high speed, where results of such operations may or may not be displayed. Generally, program modules include routines, programs, objects, components, data structures, etc. that performs particular tasks or implement particular abstract data types. As used herein, such program modules may be collectively referred to as a mobile application. As a non-limiting example, software programs that underlie embodiments can be coded in different programming languages, for use with different devices, or platforms. It will be appreciated, however, that the principles that underlie embodiments disclosed herein can be implemented with other types of computer software technologies as well.

Moreover, those skilled in the art will appreciate that embodiments disclosed herein may be practiced with other computer system configurations, multiprocessor systems, microprocessor-based or programmable consumer electronics, minicomputers, mainframe computers, and the like. Embodiment may also be practiced in distributed computing environments where tasks are performed by remote processing devices that are linked through at least one communications network. In a distributed computing environment, program modules may be located in both local and remote computer storage media including memory storage devices.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 4.

Referring now to the drawings, embodiments will be described. Embodiments can be implemented in numerous ways, including as a system (including a computer processing system), a method (including a computerized method), an apparatus, a computer readable medium, a computer program product, a computer software code, or a data structure tangibly fixed in a computer readable memory. Several embodiments, illustrating non-limiting examples, are discussed below.

As used herein physiological stress is disclosed. Physiological or biological stress may be considered an organism's response to a stressor such as an environmental condition or a stimulus. Stress is a body's method of reacting to a challenge. According to the stressful event, the body's way to respond to stress is by sympathetic nervous system activation which results in the fight-or-flight response. In humans, stress typically describes a negative condition or a positive condition that can have an impact on a person's mental and physical well-being. The embodiments below disclose embodiments which are not limited to a laboratory or confined location, such as, but not limited to, an examination room. As should be appreciated, stress triggering events are unpredicted as they may occur in the current environment where the user is located. The embodiments disclosed herein provide for being able to ascertain when stress is experienced regardless of the location of the user as sensors to measure characteristics of the user and device to evaluate the characteristics to determine stress are available for mobility and ease of use.

Overview

A system, designated as mCALM by the inventors, is designed to improve the quality and efficiency of therapy of an individual by substantially increasing a medical provider's insight into distress events experienced by the individual, or patient, during treatment. Such insight may include real-time data of distress events, triggers, mitigations employed, and physiological response is captured and summarized for the patient. This comprehensive treatment support tool may be used in isolation and/or in support of ongoing therapist-driven treatment to improve tracking, effectiveness, and efficiency of treatment.

Figure 1:
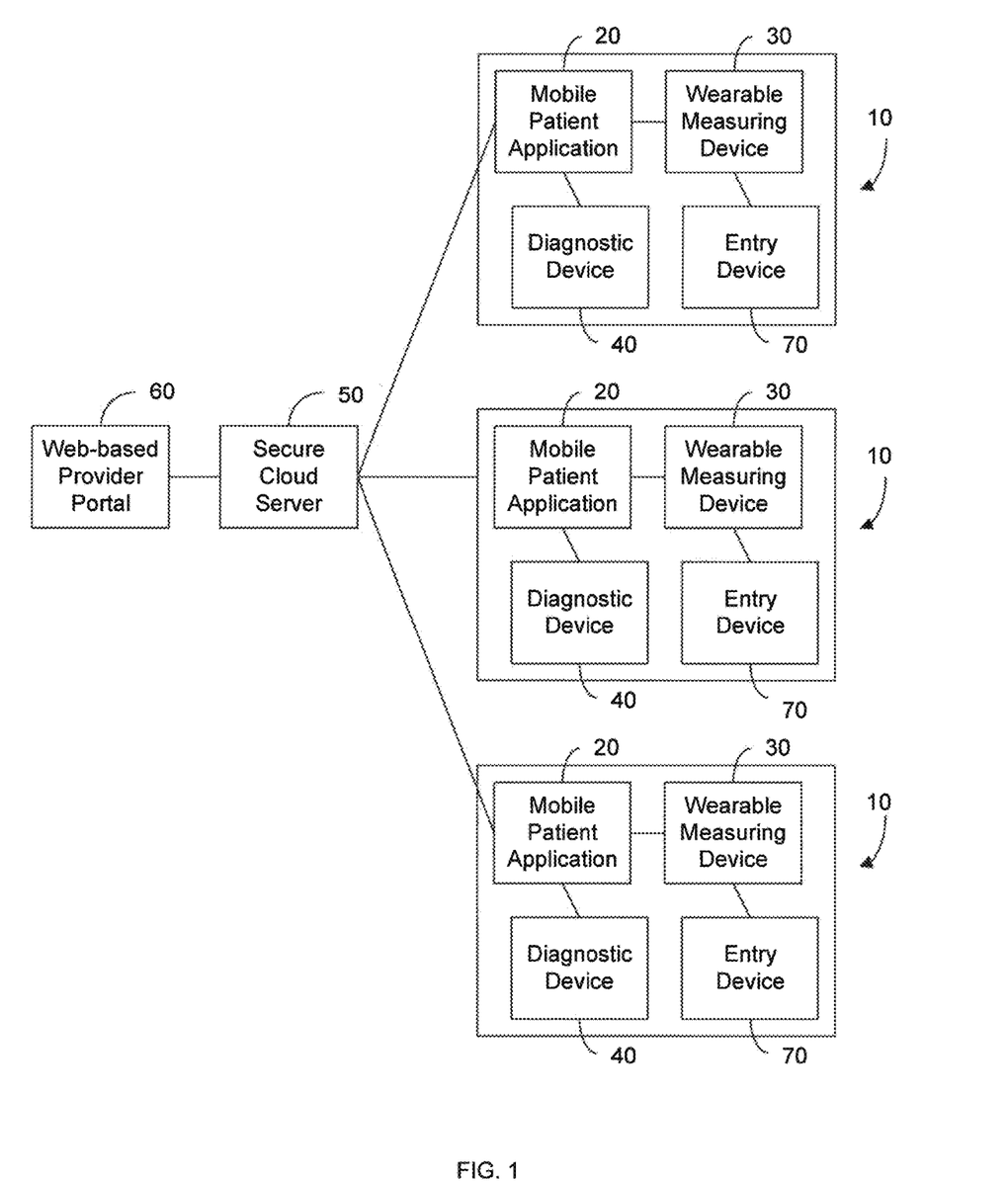
FIG. 1 discloses a block diagram illustrating an embodiment of a system for data capture, classification, and presentation based on information obtained from a user.

FIG. 1 discloses a block diagram illustrating an embodiment of systems for data capture, classification, and presentation based on information obtained from users wearing a measuring device and using a mobile application. As illustrated in FIG. 1, the mCALM system 10 may incorporate a mobile application 20, a wearable measuring device 30 (wearable physiological sensor device, or wearable sensor array), and a diagnostic device 40. The mobile application 20, in conjunction with the wearable physiological sensor device 30, may track and assess physiological and contextual indicators of stress, capture subjective emotional states and triggers associated with these events, deliver biofeedback to users to increase awareness of non-optimal arousal states, and trigger real-time evidence-based strategies for addressing periods of stress. A diagnostic device 40 is also disclosed. The diagnostic device 40 compares real-time physiological data to pre-determined baseline levels to indicate times when a given threshold is exceeded, thus indicating periods of stress.

As used herein, real-time may be based on a minute-to-minute comparison where real-time is based on a minute as its period. As such, the sensor device 30 may be able to collect data within this time period. As such, as a non-limiting example, an accelerometer may have a minimum sampling rate of approximately 32 hertz ("Hz"), the heart rate sensor may have a minimum sampling rate of approximately 64 Hz, the temperature sensor may have a minimum sampling rate of approximately 4 Hz, and the skin conductance sensor may have a minimum sampling rate of approximately 4 Hz.

The wearable measuring device 30 may comprise at least one sensor that collects data from the user based on being in contact with the user's skin or proximate to the user's skin wherein proximate is meant to mean within about one centimeter. Non-limiting examples of the type of data that may be collected include, but are not limited to, heart rate, skin conductance, skin temperature, and movement of the user. Thus, non-limiting examples of at least one sensor may comprise a heart rate monitor, a sensor to measure electrical conductance of the skin, which varies depending on the amount of sweat-induced moisture on the skin, a skin temperature sensor, and an accelerometer.

As further illustrated in FIG. 1, information or data collected may be communicated to a storage device 50, such as, but not limited to, a secure cloud server. In a non-limiting example, the information or data collected may be stored for comparing recently acquired information with information or data acquired previously. The mobile application 20 may also support treatment reminders from a medical provider, such as, but not limited to a counselor, psychologist, psychiatrist, etc. Such reminders may be accomplished by providing a communication portal 60, such as, but not limited to a web-based provider portal through which the provider may review the data in the server 50. In an embodiment, the mobile application 20 may provide biofeedback of physiological state to increase awareness of stress onset, provide the user with individualized evidence-based treatment techniques designed to reduce symptoms of distress the user is experiencing, and send data via Bluetooth. Thus, the portal 60 provides two-way communication, since the provider is able to monitor data collected and stress incidents, and provide directions to the user. As a non-limiting example, if a recurring level of stress levels is above a certain threshold, the provider may send a message, which may appear as a text message through the wearable measuring device 30, visible to the user. In another non-limiting example, the message may be communicated to a mobile phone which may operate in conjunction with the wearable device 30. In a non-limiting example, the secure cloud server may be a mobile phone which operates in conjunction with the wearable measuring device 30.

As further disclosed below, the system 10 may further comprise an entry, or input, device 70 through which the user may acknowledge, or designate, when the user is experiencing stress. The entry device may be located on the wearable measuring device 30 or may be located on a mobile device that may be used in association with the wearable measuring device 30.

Figure 2:
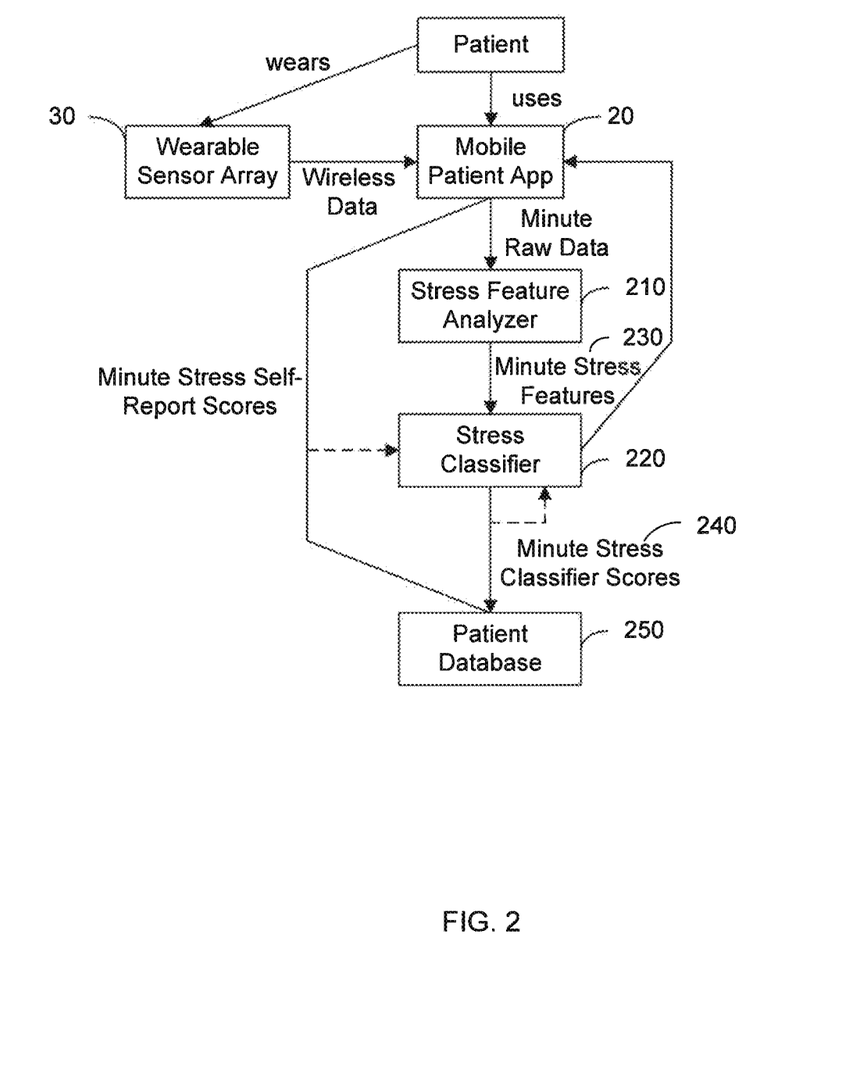
FIG. 2 shows a flowchart illustrating an embodiment of an overview of information flow through a classifier system.

FIG. 2 shows an embodiment of a stress classification system. The user, patient, or subject may wear the wearable sensor array 30 and using the mobile patient application 20 may monitor their stress levels in real-time. In a non-limiting example, the mobile patient application 20 may reside on a mobile device, such as, but not limited to, a mobile phone (Smartphone) or tablet where the user may use the mobile device to monitor their stress levels in real-time. In another non-limiting example, the user may actually use a display on the wearable measuring device 30 to monitor their stress levels in real-time.

As a non-limiting example, the mobile patient application 20 may implement two components for classifying the patient's stress levels on a minute-by-minute basis. A first component may be a stress feature analyzer 210 which may read in a 1-minute block of raw sensor data and output a set of stress features for that minute A second component may be a stress classifier 220 that may read the minute stress features 230 provided from the stress feature analyzer 210 and may output a minute stress classifier score 240 to a patient database 250, which may be located on the secure cloud server 50, which may keep track of the patient's self-reported and classifier-reported stress during the minutes the mobile patient application 20 and sensor device 30 are being used, and may also output alerts to the patient when some threshold level of stress occurs.

In an embodiment, in operation the system 10 may first be trained by the patient running a calibration phase where the patient may sit quietly and relax, allowing the sensors to capture the patient's baseline heart rate and skin conductance levels. During normal operation, the classifier 220 makes a determination of stress relative to these baseline references. In addition, the stress classifier 220 may contain an adaptation component 460, which may be, but is not limited to being, an adaptation algorithm, that permits discrepancies in self-reported stress, entered with the entry device 70, and classifier-reported stress to reset a bias/threshold in the constituent classifiers allowing lesser or greater sensitivity to heart rate and skin conductance signals. The result is a stress classifier with some capacity to adapt its sensitivity to particular individuals.

Data collection from the wearable sensory array 30 may be done via the mobile patient application 20. Based on the sensors discussed above, one data modality may include a cardiovascular activity signal, such as, but not limited to, a blood pulse volume ("BVP") signal which uses photoplethysmography ("PPG") to read the degree of blood oxygenation in the area of skin touched by the sensor, electrocardiogram ("EGG") to assess heart electrical activation, or pressure-based methods to assess pulse. Other data modalities may include an electrodermal activity ("EDA") signal, which is the measure of current conductance through the area of skin touched by the sensor electrodes, accelerometer signals which indicate the direction of acceleratory motion of the device, and a skin temperature signal, which is used to estimate body temperature. Samples from these sensors may be uniformly or non-uniformly sampled. The data collection process may merely bundle the samples into (non-overlapping) minute blocks to allow feature analysis on a minute-by-minute basis.

Briefly, the cardiovascular activity signal and EDA signals may be used to measure heart-rate ("HR") and skin conductance, respectively. When one or both of these features are sufficiently high, it may be used as an indicator of increased stress level. However, HR and EDA (through sweating) may also increase with vigorous movement, which suggests that during significant movement the classification approach could be inaccurate. When the ambient temperature is high, also, EDA will increase through thermoregulatory sweating, necessitating the inclusion of a heat classifier that can also deactivate overall stress classification in high temperature environments.

Figure 3:
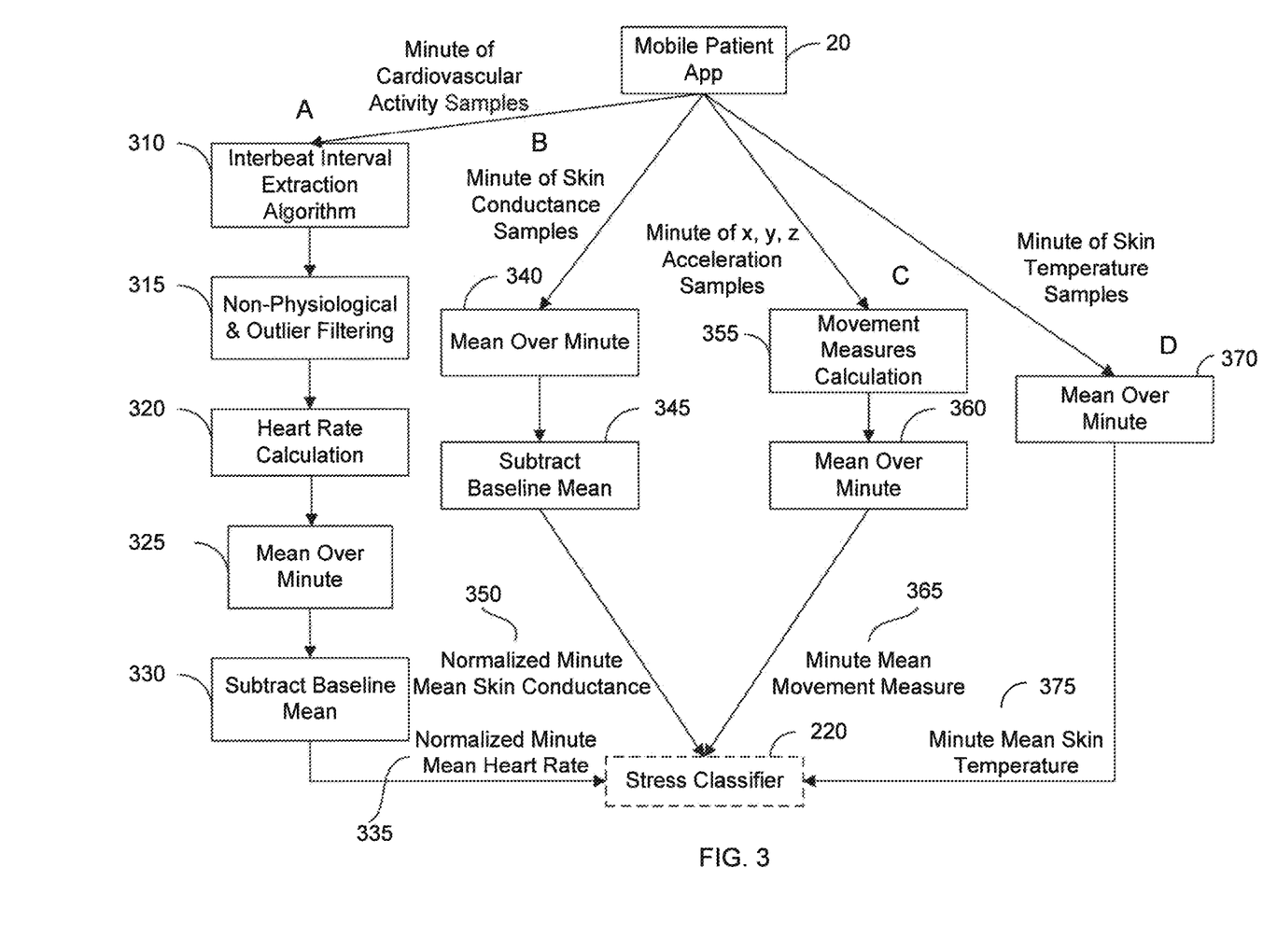
FIG. 3 shows an embodiment of information flow for feature extraction.

FIG. 3 shows an embodiment of stress feature extraction processes. As illustrated, there may be four parallel channels of feature extraction in the stress feature analyzer 210 that read in minute-blocked raw samples for, respectively cardiovascular activity (A), EDA (skin conductance) (B), x, y, and z acceleration (C), and skin temperature (D). Each channel A, B, C, D are explained in further detail below.

Heart-Rate Feature Extraction

Measures of cardiovascular activity may fluctuate according to the state of the heart's pumping. As a non-limiting example, the blood volume pulse PPG signal may fluctuate according to an amount of oxygenated blood in the tissue under the sensor. A peak in the amplitude of this signal may correspond with the propagation of arterial blood from the heart to the area of skin where the measurement is taken, so the temporal distance between peaks of this signal may correspond with the heart's interbeat interval ("IBI"). Whatever cardiovascular activity signal is used, the first processing step is to extract the IBIs, at 310. As a non-limiting example, a prior art approach may involve calculating a derivative of the original time series and using the result to extract the locations of the original signal's peaks. This may be accomplished by starting at the beginning of the signal, finding the leading edge of a peak, by finding the derivative over some positive threshold, and then locating the peak by finding the next zero derivative point. Elimination of local maxima in the signal that are not true heart-beat peaks may also be provided for. Although the algorithm was developed with PPG signals in mind, the algorithm may possibly be used on other pulse-measures of heart activity, and for ECG there are standard algorithms for extracting IBI.

Once IBIs are extracted for the minute, the next step is non-physiological and outlier filtering, at 315. This may be accomplished to remove IBIs that are outside the range of normal human physiology. For adults, band limits at about 0.33 seconds and about 1.5 seconds, which correspond, respectively, to heart-rates of about 180 and about 40 beats per minute, which may be sufficient for general stress classification. The next step in the filtering process may be to remove outliers, which in our current implementation may be cut off when an IBI lies outside 2 standard deviations of the mean. If less than some minimum number of samples remain after filtering, then the rest of the data may be thrown out and the HR estimate for the minute may be flagged as missing.

A heart rate calculation, at 320, is completed with the remaining IBI samples may be converted into heart rates in units of bpm, which may be done by dividing the IBI values from 60.0 seconds. Then, the IBIs in the minute's sample may be averaged (determining a mean), as identified as mean over minute, at 325. If the classifier system is being calibrated, these mean HRs, taken during the Patient's relaxation period, may be saved and averaged together to give a baseline mean HR. During normal operation of the classifier system, this remembered baseline HR may be subtracted, at 330, from the mean minute HR as the last step in the HR feature extraction process. The normalized minute mean heart rate, at 335, is then provided to the stress classifier 220.

Skin Conductance Feature Extraction

The feature extraction for the EDA signal may involve taking the mean of the conductance samples during the minute, at 340. If the classifier system is being calibrated, these mean EDAs, taken during the Patient's relaxation period, may be saved and averaged together to give a baseline mean EDA. During normal operation of the classifier system, this remembered baseline EDA may be subtracted from the mean minute EDA, at 345 as the last step in the skin conductance feature extraction process. The normalized minute mean skin conductance, at 350 may then be provided to the stress classifier 220.

Movement Feature Extraction

A first step in the feature extraction process for movement may be to convert all of the multi-axis accelerations detected during the minute into a measure of amplitude of movement, at 355. If the accelerations $a_x$, $a_y$, and $a_z$ at a given time are given in terms of the units of the gravitational acceleration constant g, then the movement measure used is defined as $$m(t) = |\sqrt{a_x^2 + a_y^2 + a_z^2} - 1.0|$$

This means that the modulus of the acceleration vector is taken and, effectively, g is subtracted out leaving the non-gravitational component of the acceleration. This signal may be rectified (i.e., absolute value taken) in order to treat accelerations in either direction as being positive instances of movement.

The last step of movement feature extraction may be to average over the minute all of the m(t) values, at 360. A minute mean movement measure feature 365 is then provided to the stress classifier 220.

Skin Temperature Feature Extraction

The feature extraction for the skin temperature signal may involve taking the mean of the temperature samples during the minute, at 370. A minute mean skin temperature 375 is then provided to the stress classifier 220.

Figure 4:
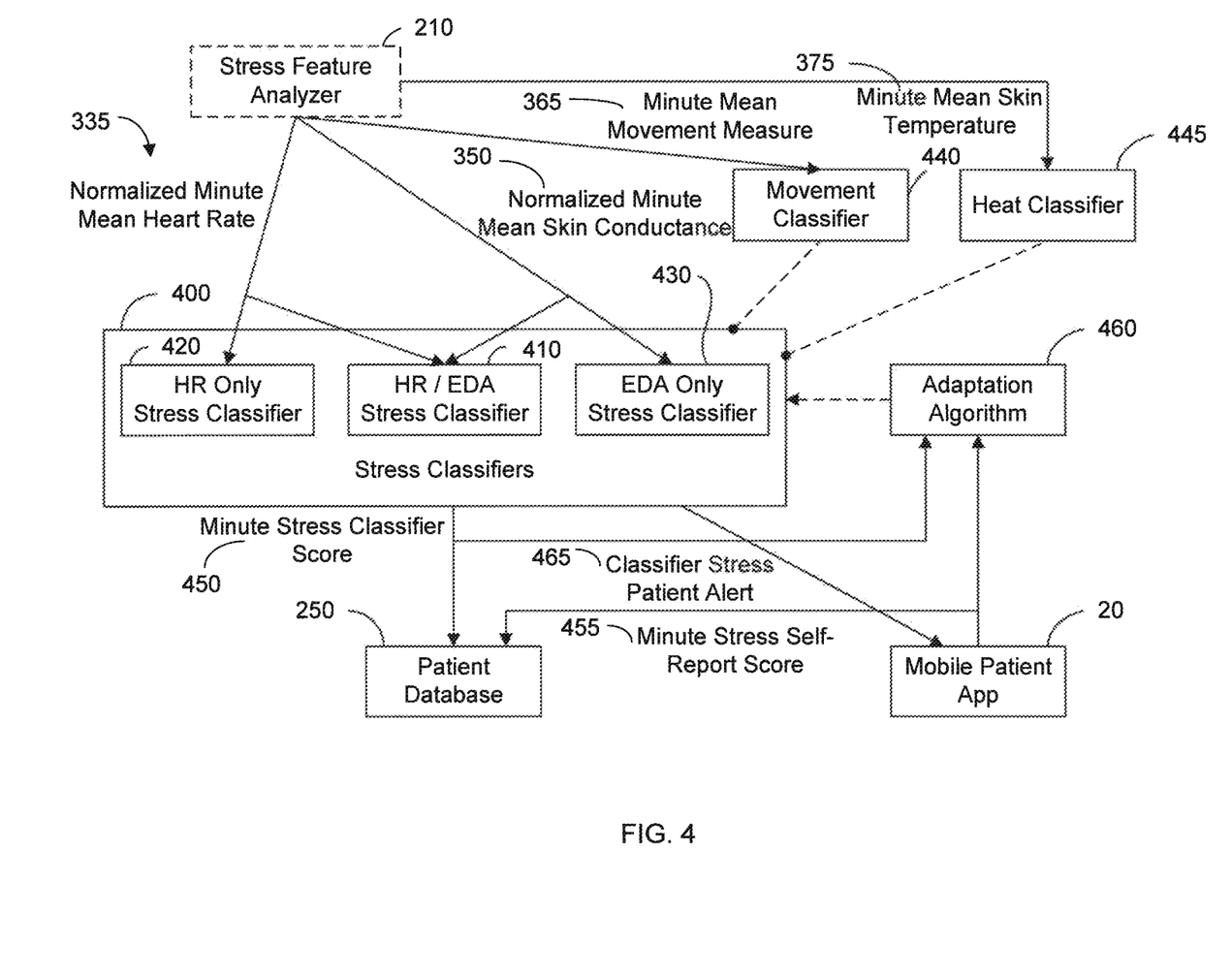
FIG. 4 shows processes entailed by a classifier portion of the system.

FIG. 4 shows the processes entailed by the classifier portion of the system. As illustrated in FIG. 4, the minute features from the feature analyzer 210 may be passed to the stress classifier 220 which may comprise a set of classifiers. Classification features that are used within at least one set of classifiers may include the Normalized Minute Mean Heart Rate feature 335, Normalized Minute Mean Skin Conductance feature 350, Minute Mean Movement Measure feature 365, and Minute Mean Skin Temperature feature 375. As a non-limiting example, three separate stress classifiers 400 may be used to score stress based on baseline-normalized FIR and EDA. The main classifier, whose results may be used when both HR and EDA data are available for the minute, is a HR/EDA Stress Classifier 410. As illustrated, the HR/EDA Stress classifier 410 may include the Normalized Minute Mean Heart Rate feature 335 and the Normalized Minute Mean Skin Conductance feature 350. When EDA data is missing for the minute, then a HR Only Stress Classifier 420 may be used instead. The HR Only Stress Classifier 420 may include the Normalized Minute Mean Heart Rate feature 335. When HR data is missing, an EDA Only Stress Classifier 430 may be used. The EDA Only Stress Classifier 430 may include the Normalized Minute Mean Skin Conductance feature 350. All three of these classifiers 410, 420, 430 may be deactivated when either movement or heat conditions are detected using a movement classifier 440 and a heat classifier 445, respectively. These two ancillary classifiers may each use a single minute feature from the Stress Feature Analyzer. As illustrated, the movement classifier 440 may use the Minute Mean Movement Measure feature 365 and the heat classifier 445 may use the Minute Mean Skin Temperature feature 375.

Figure 5:
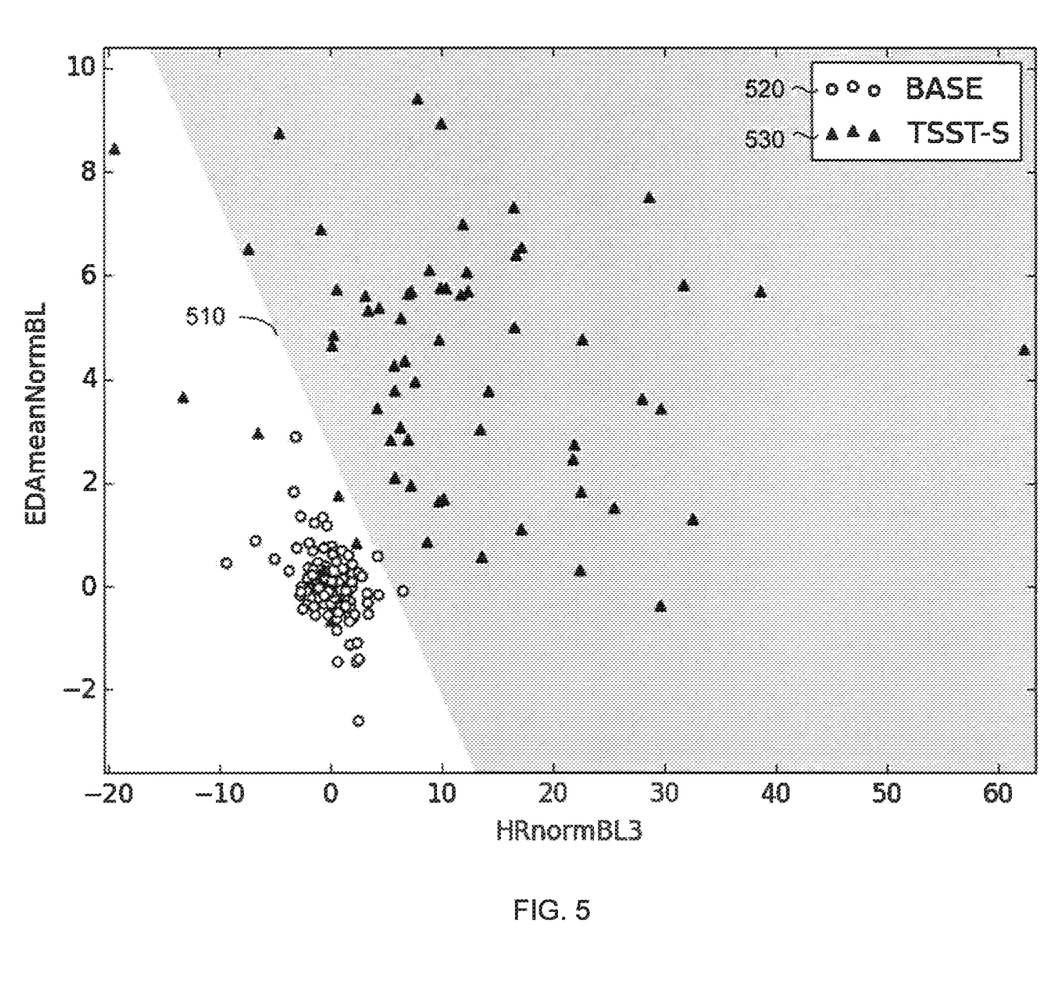
FIG. 5 shows an embodiment of classification of physiological stress based on plotted data points for multiple individuals.

All five of these classifiers may be linear boundary classifiers, as illustrated in FIG. 5, which may be provided to classify on one or two features and trained using supervised learning on truth-tagged data sets. The respective stress classifiers may be trained using a corpus of Stress/Non-Stress HR and EDA data.

When the stress classifiers are not deactivated, the one which is active may emit a real-valued score, where the decision boundary is at 0.0, where Non-Stress is indicated by negative values, and Stress is indicated by positive values. For each of these classifiers, a set of 10 real-valued "attractor points" may be used to convert the real value into a 1-to-10 integer-valued stress score. The integer that is the index of the 'attractor' that is the nearest neighbor of the real-valued classifier score becomes the integral score value. For a given minute, the patient database 250 may store the current minute stress classifier score 450 and any corresponding minute stress self-report score 455 entered by the patient. Additionally, if the minute stress classifier score 450 is over some threshold, a classifier stress patient alert 465 may be sent to the user through the mobile patient application, possibly prompting a self-report to be made which could adjust classifier sensitivity and prompt therapeutic relaxation exercises implemented on or suggested by the mobile patient application.

Linear Classifiers

For each linear classifier 410, 420, 430, there may be two stages of processing that are used to transform minute features from the stress feature analyzer 210 into the generated real-valued stress scores. First, the features may be normalized by subtracting a mean value μ and then dividing by a standard deviation σ. These values may be fit to the entirety of the training set. After this normalization, the features may be then fed into a linear classifier that effectively takes the dot product of the features with a set of learned weight, one per feature, and then may add a learned bias term. As a non-limiting example, for the HR/EDA stress classifier the normalizer consists of the following equations:

$$\tilde{x}_{HR} = \frac{x_{HR} - \mu_{HR}}{\sigma_{HR}}$$

$$\tilde{x}_{EDA} = \frac{x_{EDA} - \mu_{EDA}}{\sigma_{EDA}}$$

These may scale the Normalized Minute Mean Heart Rate ($x_{HR}$) and Normalized Minute Mean Skin Conductance ($x_{EDA}$), respectively, into the coordinates of the HR/EDA classifier, which is then defined by the following formula:

$$s = w_{HR}\tilde{x}_{HR} + w_{EDA}\tilde{x}_{EDA} + b_{HR+EDA}$$

Here $\tilde{x}_{HR}$ and $\tilde{x}_{EDA}$ are the normalized features, $w_{HR}$ and $w_{EDA}$ are the corresponding weights learned by the classifier and $b_{HR+EDA}$ is the bias learned by the classifier. If s>0 then the classifier makes a positive classification of Stress; otherwise the classifier makes a negative classification (Non-Stress). Stochastic gradient descent may be used for learning weights and biases, but a variety of machine learning algorithms could be used for the training.

FIG. 5 shows an embodiment of classification of physiological stress based on plotted data points for multiple individuals from the training corpus. To develop a classifier which provides accurate stress detection, a way to estimate/learn the weight and bias parameters was required. To do so, set data or "ground truth" data was evaluated with a supervised learning algorithm which could learn specific values of parameters that may provide the classifier with a desired performance on novel data, namely data that may come up from the user of the device. To get this "ground truth" data, the inventors ran a human subjects experiment in which heart and skin conductance physiological measures were recorded when the subject was at rest. When the human subjects were engaged in a task, such as, but not limited to, simulated public speaking, that is known to induce stress, measurements were taken. A decision boundary 510 is illustrated where some test data from a larger subset of the subjects is run through the classifier 410. As illustrated, there were two kinds of data-points run through the classifier 410. One kind are those that come from when the subject was at rest, or baseline or base data 520. The other kind is when the subjects were engaged in an activity, such as, but not limited to, speaking as identified by TSST-S data 530. Though there are both kinds of points on both sides of the decision boundary, generally, it is desirable that the Base data 520 be on the left side of the boundary 510 and the TSST-S data 530 be on the right side of the boundary 510.

Illustrated is a typical decision boundary defined by a 2-feature linear classifier. The HR only classifier 420, EDA only classifier 430, movement classifier 440, and heat classifier 445 may be similar in their construction, but use only one rather than two features, where the equations may take the form:

$$\tilde{x}_{feat} = \frac{x_{feat} - \mu_{feat}}{\sigma_{feat}}$$

$$s = w_{feat}\tilde{x}_{feat} + b_{feat}$$

During operation of the classifier system, parameters of the respective classifiers may all remain fixed with the possible exception of the bias parameters which may be adjusted by an adaptation algorithm 460 described next.

The adaptation algorithm block 460, as illustrated in FIG. 4 may compare, when the data is available, the 1-to-10 integer-valued stress self-report for a minute with the 1-to-10 integer-value reported by the stress classifiers 410, 420, 430. If self-reported stress scores are frequently greater than classifier scores, suggesting the classifier is not sensitive enough, then the biases of the classifier 220 may be raised to make the classifiers 410, 420, 430 more sensitive to heart rate and skin conductance. In an embodiment, if self-reported stress scores are frequently less than classifier scores, suggesting an over-sensitive classifier, then the biases of the stress classifiers 410, 420, 430 may be lowered to make them less sensitive to heart rate and skin conductance.

Figure 6:
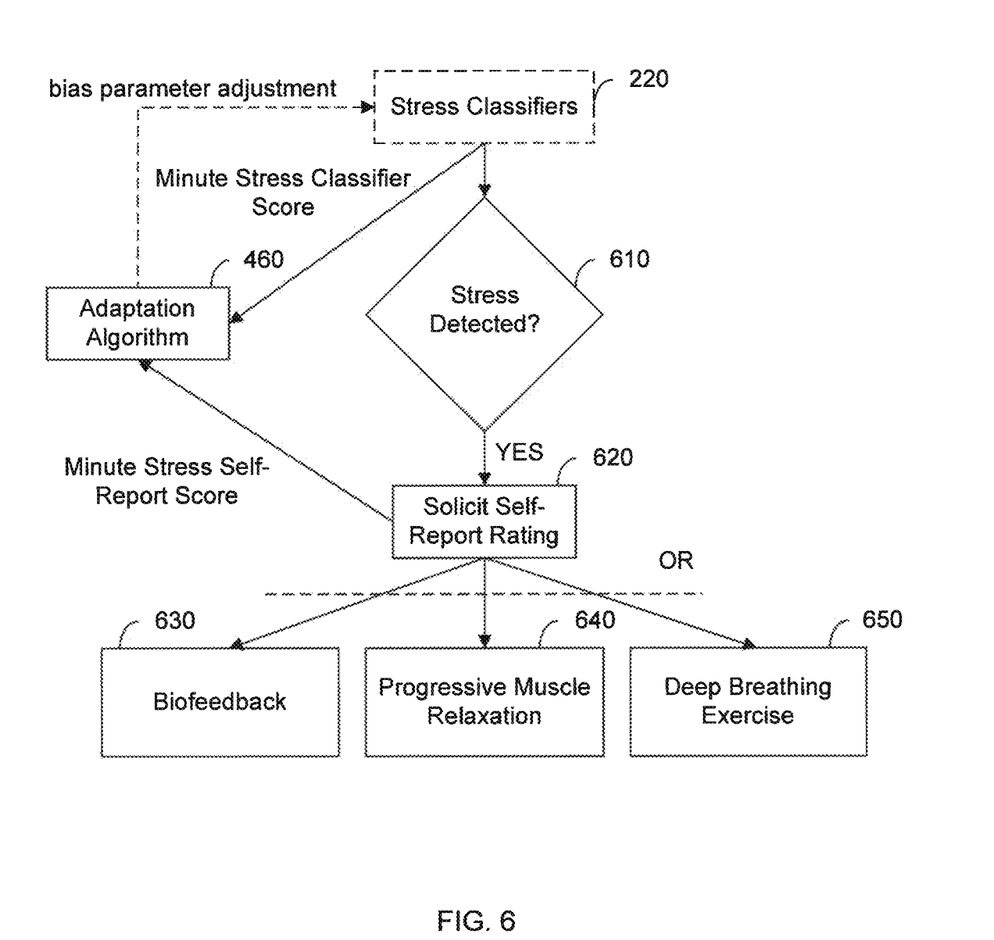
FIG. 6 shows mitigations when stress is detected.

FIG. 6 shows mitigations when stress is detected. When stress is detected, at 610 by the stress classifier 220, a notification may be sent to the patient mobile application 20 to prompt the user for a self-report rating on a 1-10 scale, at 620. This rating may then be paired to the 1-10 Objective classifier rating and the adaptation algorithm 460 bias parameter may be adjusted to create a personalized detection threshold for the patient. In a non-limiting example, if the patient reports a subjective stress rating of 4 or higher, the mobile application 20 may prompt the user to complete a relaxation strategy. As illustrated, at least one of three relaxation strategies may be provided, including, but, not limited to, biofeedback 630, progressive muscle relaxation 640, and guided deep breathing 650. The prompt may be provided on at least one of the mobile device and the wearable device 30 where the prompt may be audible or visible. As a non-limiting example, the audible prompt may provide a particular sound emitted which is associated with a particular relaxation strategy. The visible prompt may be an image on a screen of the mobile device or wearable device 30. In an embodiment, both an audible and visible prompt are provided where the audible prompt may notify the user to look at the visible prompt.

Figure 7:
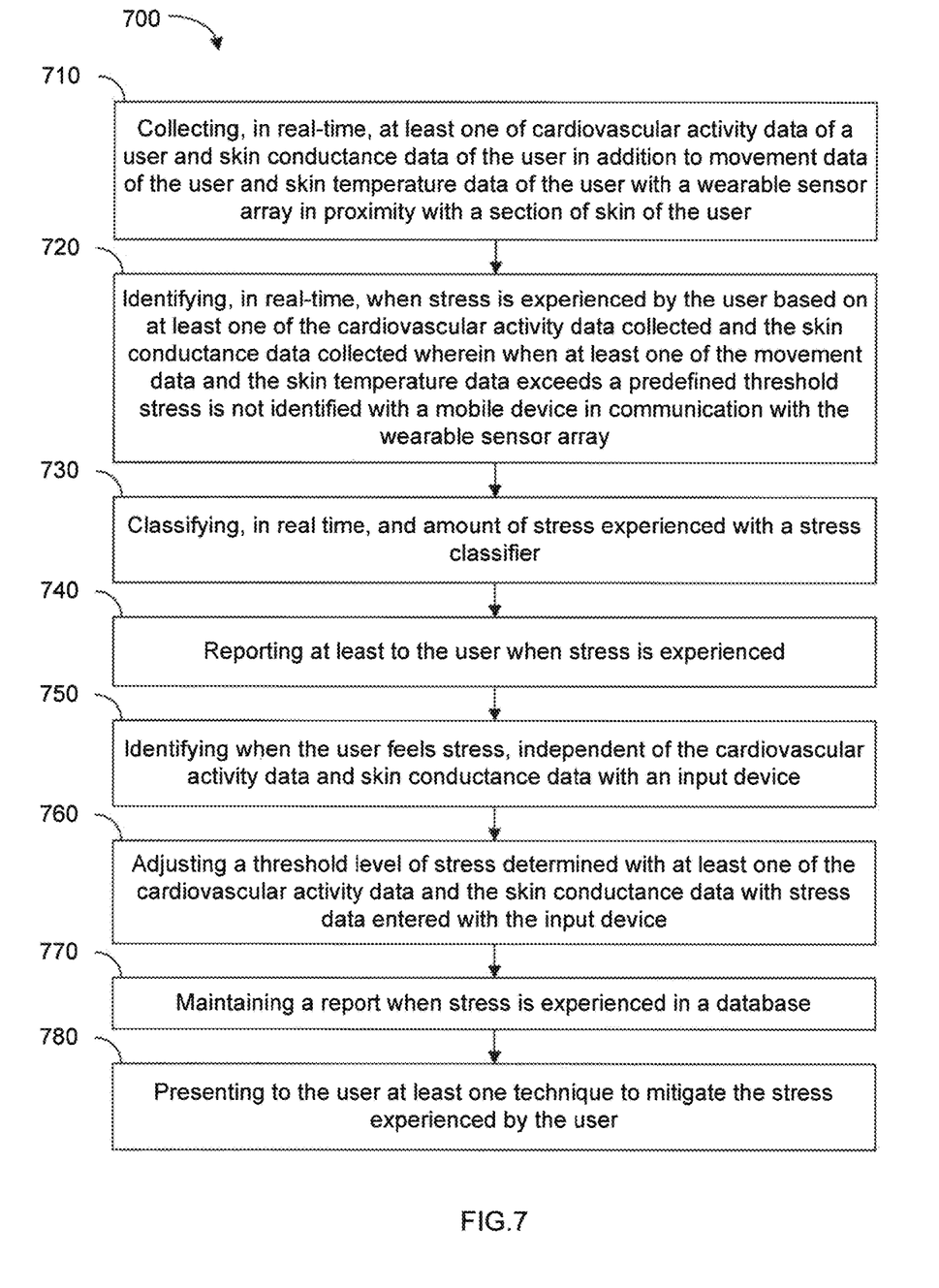
FIG. 7 shows flowchart illustrating an embodiment of a method.

FIG. 7 shows flowchart illustrating an embodiment of a method. The method 700 comprises collecting, in real-time, at least one of cardiovascular activity data of a user and skin conductance data of the user in addition to movement data of the user and skin temperature data of the user with a wearable sensor array in proximity with a portion or section of skin of the user, at 710. The method 700 further comprises identifying, in real-time, when stress is experienced by the user based on at least one of the cardiovascular activity data collected and the skin conductance data collected wherein when at least one of the movement data and the skin temperature data exceeds a predefined threshold stress is not identified with a mobile device in communication with the wearable sensor array, at 720. The method also comprises classifying, in real time, an amount of stress experienced with a stress classifier, at 730, and reporting at least to the user when stress is experienced, at 740. Reporting, at 740 may also occur in real time.

The method may further comprise identifying when the user feels stress, independent of the cardiovascular activity data and skin conductance data with an input device, at 750. The method 700 may further comprise adjusting a threshold level of stress determined with at least one of the cardiovascular activity data and the skin conductance data with stress data entered with the input device, at 760. The method may further comprise maintaining a report when stress is experienced in a database, at 770. The method 700 may further comprise presenting to the user at least one technique to mitigate the stress experienced by the user, at 780.

Though the steps are shown in a particular order, this order is not limiting. Furthermore, dependent steps 750, 760, 770, and 780 may be performed without the need of the other dependent steps.

In view of the above, a non-transitory processor readable storage medium is provided. The storage medium comprises an executable computer program product which further comprises a computer software code that, when executed on a processor, causes the processor to perform certain steps or processes. Such steps include, but are not limited to, causing the processor to identify, in real-time, when stress is experienced by the user based on at least one of cardiovascular activity data collected and skin conductance data collected with a wearable sensor array proximate the skin of the user; cease to identify, in real-time, when stress is experienced when at least one of movement data collected and the skin temperature data collected with the wearable sensor array proximate the skin of the user exceeds a predefined threshold; classify, in real time, an amount of stress experienced; and report at least to the user when stress is experienced.

The terminology used herein is for the purpose of describing particular embodiments only and is not intended to be limiting. As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising." Moreover, unless specifically stated, any use of the terms first, second, etc., does not denote any order or importance, but rather the terms first, second, etc., are used to distinguish one element from another.

Unless otherwise defined, all terms (including technical and scientific terms) used herein have the same meaning as commonly understood by one of ordinary skill in the art to which embodiments belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

While various disclosed embodiments have been described above, it should be understood that they have been presented by way of example only, and not limitation. Numerous changes, omissions and/or additions to the subject matter disclosed herein can be made in accordance with the embodiments disclosed herein without departing from the spirit or scope of the embodiments. Also, equivalents may be substituted for elements thereof without departing from the spirit and scope of the embodiments. In addition, while a particular feature may have been disclosed with respect to only one of several implementations, such feature may be combined with one or more other features of the other implementations as may be desired and advantageous for any given or particular application. Furthermore, many modifications may be made to adapt a particular situation or material to the teachings of the embodiments without departing from the scope thereof.

Therefore, the breadth and scope of the subject matter provided herein should not be limited by any of the above explicitly described embodiments. Rather, the scope of the embodiments should be defined in accordance with the following claims and their equivalents.

We claim:

1. A system comprising:
   a measuring device comprising sensors configured to collect data from a user based on the sensors being at least one of in contact with and proximate to a section of skin of the user;
   a stress feature analyzer configured to determine a cardiovascular activity feature of the user, a skin conductance feature of the user, movement of the user, and skin temperature of the user based on the data collected with the measuring device; and
   a stress classifier configured to classify and report stress experienced by the user based on at least one of one feature selected from the cardiovascular activity feature and the skin conductance feature, and two features including a combination of the cardiovascular activity feature and the skin conductance feature, the stress classifier includes:
      a first stress classifier to classify the stress experienced by the user based on the one feature being the cardiovascular activity feature for a minute time interval when skin conductance data is missing during the minute time interval;
      a second stress classifier to classify the stress experienced by the user based on the one feature being the skin conductance feature for the minute time interval when cardiovascular activity data is missing; and
      a third stress classifier to classify the stress experienced by the user based on the two features including the combination of the cardiovascular activity feature and the skin conductance feature during the minute time interval when both the cardiovascular activity data and the skin conductance data are available;
   wherein when at least one of the skin temperature and movement of the user exceeds a defined threshold, the first, the second and third stress classifiers cease classify the stress experienced by the user.

2. The system according to claim 1, further comprising a database configured to maintain the report.

3. The system according to claim 1, further comprising:
   an input device configured to allow the user, by self-reporting, to designate when psychological stress is experienced; and
   an adaptation component including an adaptation algorithm wherein the stress classifier makes a determination of the stress experienced by the user relative to baseline references and to reset a bias threshold to allow lesser or greater sensitivity to heart rate of the cardiovascular activity feature or the skin conductance feature of the user.

4. The system according to claim 1, wherein the measuring device is a part of a wearable device and at least one of the stress feature analyzer and the stress classifier are part of a mobile device which is in communication with the wearable device.

5. The system according to claim 1, wherein the stress feature analyzer and the stress classifier determine the stress experienced by the user in real-time on a minute-to-minute basis.

6. The system according to claim 1, further comprising a display configured to show a stress score generated by the stress classifier wherein the stress score representative of the stress experienced by the user.

7. The system according to claim 6, wherein the display is further configured to show at least one technique to mitigate the stress experienced by the user.

8. The system according to claim 1, wherein the stress feature analyzer is configured to, when determining the cardiovascular activity feature:
    identify an interbeat interval data of a heart of the user based on cardiovascular activity data collected;
    filter the interbeat interval data that is outside of a defined range;
    convert a non-filtered interbeat interval data into heart rates;
    average the heart rates over a period used to define real-time to determine a mean heart rate; and
    determine a baseline heart rate when the user is at rest, and subtract the baseline heart rate from the mean heart rate to determine a normalized minute mean heart rate wherein the normalized minute mean heart rate is the cardiovascular activity feature used by the stress classifier to ascertain the stress experienced by the user.

9. The system according to claim 1, wherein the stress feature analyzer configured to:
    determine a mean skin conductance based on a mean of skin conductance data collected over a period used to define real-time;
    determine a baseline skin conductance based on the skin conductance data collected when the user is at rest; and
    subtract the baseline skin conductance from the mean skin conductance to determine a normalized minute mean skin conductance wherein the normalized minute mean skin conductance is the skin conductance feature used by the stress classifier to ascertain the stress experienced by the user.

10. A method comprising:
    collecting, in real-time, at least one of cardiovascular activity data of a user and skin conductance data of the user in addition to movement data of the user and skin temperature data of the user with a wearable sensor array in proximity with a section of skin of the user;
    classifying, in real-time, by a stress classifier, stress experienced by the user based on at least one of the cardiovascular activity data collected and the skin conductance data collected wherein the classifying, by the stress classifier, the stress experienced by the user comprises:
        classifying by a first stress classifier, the stress based only on one feature being a cardiovascular activity feature based on the cardiovascular activity data collected for a minute time interval when the skin conductance data is missing during the minute time interval;
        classifying by a second stress classifier, the stress based only on one feature being a skin conductance feature based on the skin conductance data for the minute time interval when the cardiovascular activity data is missing; and
        classifying by a third classifier, the stress based on a combination of the cardiovascular activity feature and the skin conductance feature during the minute time interval when both the cardiovascular activity data and the skin conductance data are available;
    wherein when the skin temperature data of the user exceeds a predefined threshold the first, the second and third stress classifiers cease to classify;
    scoring, an amount of the stress experienced in response to the classified stress; and
    reporting at least to the user the amount of the stress experienced.

11. The method according to claim 10, further comprising identifying when the user feels psychological stress, independent of the physiological stress as indicated by at least one of the cardiovascular activity data and the skin conductance data with an input device.

12. The method according to claim 11, further comprising adjusting a threshold level of stress classification score determined with at least one of the cardiovascular activity data and the skin conductance data with stress data entered with the input device.

13. The method according to claim 10, further comprising presenting to the user at least one technique to mitigate the stress experienced by the user.

14. The method according to claim 10, further comprising analyzing, in real-time, the cardiovascular activity data, the analyzing comprising:
    identifying an interbeat interval data of a heart of the user based on the cardiovascular activity data collected;
    filtering the interbeat interval data that is outside of a defined range;
    converting a non-filtered interbeat interval data into heart rates;
    averaging the heart rates over a period used to define real-time to determine a mean heart rate;
    determining a baseline heart rate when the user is at rest; and
    subtracting the baseline heart rate from the mean heart rate to determine a normalized minute mean heart rate which is used to ascertain by the stress classifier the stress experienced by the user.

15. The method according to claim 10, further comprising analyzing, in real-time, the skin conductance data, the analyzing comprising:
    determining a mean skin conductance based on the skin conductance data collected over a period used to define real-time;
    determining a baseline skin conductance based on the skin conductance data collected when the user is at rest; and
    subtracting the baseline skin conductance from the mean skin conductance to determine a normalized minute mean skin conductance wherein the normalized minute mean skin conductance is used to ascertain by the stress classifier the stress experienced by the user.

16. A non-transitory processor readable storage medium, providing an executable computer program product, the executable computer program product comprising a computer software code that, when executed on a processor, causes the processor to:
    identify, in real-time, stress experienced by a user based on at least one of cardiovascular activity data collected and skin conductance data collected with a wearable sensor array proximate a section of skin of the user wherein, to identify, further causes the processor to:
    classify, by a first stress classifier, the stress based only on one feature being a cardiovascular activity feature based on the cardiovascular activity data for a minute time interval when the skin conductance data is missing during the minute time interval;

classify, by a second stress classifier, the stress based only on one feature being a skin conductance feature based on the skin conductance data for the minute time interval when the cardiovascular activity data is missing; and classify, by a third classifier, the stress based on a combination of the cardiovascular activity feature and the skin conductance feature during the minute time interval when both the cardiovascular activity data and the skin conductance data are available;

cease to identify by the first, the second and the third stress classifiers, in real-time, the stress experienced when the skin temperature data collected with the wearable sensor array proximate the section of skin of the user exceeds a predefined threshold;

score, in real-time, an amount of the stress experienced by the user; and report at least to the user the amount of the stress experienced by the user.

17. The non-transitory processor readable storage medium according to claim 16, when executed on the processor, further causes the processor to adjust a threshold level of stress determined with at least one of the cardiovascular activity data and the skin conductance data with stress data provided by the user independent of the at least one of cardiovascular activity data and the skin conductance data.

18. The non-transitory processor readable storage medium according to claim 16, when executed on the processor, further causes the processor to present to the user at least one technique to mitigate the stress experienced by the user.

19. The non-transitory processor readable storage medium according to claim 16, wherein the processor is part of a mobile device.

20. The non-transitory processor readable storage medium according to claim 16, wherein when executed on the processor, to identify, further causes the processor to: receive, via an input device, designation from the user, by self-reporting, when psychological stress is experienced; and adapting, by an adaptation component including an adaptation algorithm, a determination of the stress experienced by the user relative to baseline references and to reset a bias threshold to allow lesser or greater sensitivity to heart rate of the cardiovascular activity feature or the skin conductance feature of the user.

* * * * *